United States Patent
Mueller et al.

(10) Patent No.: US 10,130,570 B2
(45) Date of Patent: *Nov. 20, 2018

(54) KERATINOUS FIBER TREATMENT PRODUCT AND METHOD

(71) Applicant: Henkel AG & Co. KGaA, Duesseldorf (DE)

(72) Inventors: Burkhard Mueller, Duesseldorf (DE); Thorsten Knappe, Schenefeld (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,144

(22) Filed: Jun. 9, 2017

(65) Prior Publication Data

US 2017/0273878 A1 Sep. 28, 2017

Related U.S. Application Data

(63) Continuation of application No. PCT/EP2015/075375, filed on Nov. 2, 2015.

(30) Foreign Application Priority Data

Dec. 11, 2014 (DE) .................. 10 2014 225 556

(51) Int. Cl.
| | | |
|---|---|---|
| *A61Q 5/10* | (2006.01) | |
| *A61K 8/22* | (2006.01) | |
| *A45D 19/16* | (2006.01) | |
| *A61K 8/34* | (2006.01) | |
| *A61Q 5/08* | (2006.01) | |

(52) U.S. Cl.
CPC ............... *A61K 8/22* (2013.01); *A45D 19/16* (2013.01); *A61K 8/34* (2013.01); *A61Q 5/08* (2013.01); *A61Q 5/10* (2013.01); *A61K 2800/87* (2013.01)

(58) Field of Classification Search
CPC ........ A61K 8/22; A61K 8/34; A61K 2800/87; A61Q 5/08; A45D 19/16
See application file for complete search history.

(56) References Cited

U.S. PATENT DOCUMENTS

| 389,670 | A | 9/1888 | Soli |
|---|---|---|---|
| 3,790,031 | A | 2/1974 | Prussin et al. |
| 3,977,826 | A | 8/1976 | Iscowitz |
| 8,187,339 | B2 * | 5/2012 | Velazquez ............... A61Q 5/10 |
| | | | 8/405 |
| 2002/0074349 | A1 | 6/2002 | Michaels et al. |
| 2002/0079377 | A1 | 6/2002 | Nichols |
| 2004/0065683 | A1 | 4/2004 | Taylor et al. |
| 2013/0018333 | A1 * | 1/2013 | Thomason ......... A61M 35/003 |
| | | | 604/290 |
| 2013/0205515 | A1 * | 8/2013 | Misu .................... A61K 8/411 |
| | | | 8/401 |

FOREIGN PATENT DOCUMENTS

| DE | 19613941 A1 | 10/1997 |
|---|---|---|
| DE | 19756454 C1 | 6/1999 |
| EP | 2468243 A1 | 6/2012 |
| WO | 200183071 A1 | 11/2011 |

OTHER PUBLICATIONS

PCT International Search Report (PCT/EP2015/075375) dated Jan. 13, 2016.

* cited by examiner

*Primary Examiner* — Eisa B Elhilo
(74) *Attorney, Agent, or Firm* — James J. Cummings

(57) ABSTRACT

A cosmetic product includes a) a cosmetic preparation including, in relation to the total weight of the preparation, a1) 60 to 94 wt % polar solvent; a2) 0.1 to 20 wt % oxidant; and b) a device for flash-evaporating the cosmetic preparation a). A method for changing the color of keratinous fibers incorporates such a product. Particularly, the cosmetic preparation a) is used as a process material in a flash evaporation device.

20 Claims, No Drawings

KERATINOUS FIBER TREATMENT PRODUCT AND METHOD

FIELD OF THE INVENTION

The present invention generally relates to the technical field of oxidative treatment of keratinous fibers, in particular human hair. Specific cosmetic formulations for the hair, which are suitable for application to keratinous fibers by means of a flash evaporation process, form the subject matter of the application. A further subject matter of the present invention is the use of these cosmetic formulations for the hair in flash evaporation devices, as well as methods for the temporary shaping of keratinous fibers.

BACKGROUND OF THE INVENTION

An attractive hairstyle is nowadays generally regarded as an indispensable part of a well-groomed appearance. In order to achieve such an attractive hairstyle, the hair is subjected to cosmetic treatment methods ranging from cleaning by means of a shampoo to permanent shaping by means of chemical/thermal processes or permanent oxidative color lightening. For oxidative color lightening (bleaching) of the hair, use is made of aqueous oxidant preparations. These preparations can be prepared by the consumer for example in situ by mixing the required components. One point that is essential for consumer safety with this type of application method is the avoidance of product dust, in particular dust from oxidant-containing precursors.

First approaches to solving the above-described technical problems can be found in the literature. For instance, German patent application DE 19613941 A1 describes a method for producing powdered bleaching agents which do not generate dust. The bleaching agents include at least one peroxide compound, which is mixed with suitable thickeners and then packaged in portions in water-soluble pouches for transport and further processing.

The use of spraying methods for applying oxidative preparations is relatively uncommon in hair cosmetics.

The spraying systems used in hair cosmetics include in particular pump sprays or aerosol sprays, by means of which the cosmetic preparations are sprayed via a valve either by means of mechanical forces or with the aid of a propellant. Both methods have obvious disadvantages. While pump sprays are generally not suitable for a sustained and even spray application of cosmetic hair preparations, aerosol sprays are based on the use of propellants or propellant gases, which on the one hand have no cosmetic effect and on the other hand can pose a risk to consumers if not handled correctly.

Against this background, there is a need for alternative ways of atomizing cosmetic hair preparations. Flash evaporation has proven to be advantageous as one such alternative spraying method. In this method, which is described for example in international patent application WO 200183071 A1 (Henkel), a liquid or paste-like solvent-containing composition is heated in a closed chamber to a temperature above the boiling point of the solvent, thereby generating an overpressure in the composition. When the pressure is released (throttled), the liquid evaporates and can then be atomized for example by means of a suitable nozzle.

Therefore, although flash evaporation is suitable in principle for the spray application of cosmetic hair preparations, at the same time it is not possible to atomize every cosmetic hair preparation by means of a flash evaporation method. This is due on the one hand to the heating of the cosmetic preparation that is necessary for the flash evaporation, and on the other hand to the specifics of the spray mist produced by flash evaporation, for example the droplet size and droplet density produced in the spray mist.

The problem addressed by the present invention is therefore that of providing specific cosmetic hair preparations for the oxidative treatment of keratinous fibers, which on account of their chemical and physical properties are suitable for targeted spray application by means of a flash evaporation device. The preparations are also intended to be suitable for achieving a good cosmetic effect after application by means of a flash evaporation method. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is thus a cosmetic product, which includes a) a cosmetic preparation including, in relation to the total weight of the preparation, a1) 60 to 94 wt % polar solvent;

a2) 0.1 to 20 wt % oxidant;

b) a device for flash-evaporating the cosmetic preparation a).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been found that, among the many known cosmetic hair preparations, solvent-containing preparations having specific proportions by weight of oxidants are particularly suitable for solving the above-mentioned problems.

The cosmetic preparation a) is liquid. The cosmetic preparation a) may exist as a solution or dispersion, for example as an emulsion or suspension. Preferred cosmetic preparations a) are in the form of a solution or a suspension.

The cosmetic preparation according to the invention includes, as a first essential constituent, 60 to 94 wt % of a polar solvent a1). Preferred cosmetic products are characterized in that the proportion by weight of the polar solvent a1) in relation to the total weight of the cosmetic preparation a) is 65 to 90 wt %, preferably 70 to 88 wt % and in particular 75 to 85 wt %. Such products are characterized by a good cosmetic effect while at the same time being easy to apply.

In order to improve the application properties of cosmetic preparations according to the invention while at the same time minimizing the thermal stress of any active ingredients or auxiliaries in the course of the flash evaporation process, it has proven to be advantageous to use polar solvents a1) which have a boiling temperature (20° C. and 1013 mbar) between 50 and 110° C., preferably between 70 and 105° C. Ethanol and water have proven to be particularly suitable, and for this reason they are preferred as polar solvents a1).

Particularly preferred polar solvents a1) or solvent systems are polar solvents a1) in which the proportion by weight of water in relation to the total weight of the polar solvent a1) is more than 80 wt %, preferably more than 85 wt % and in particular more than 90 wt %.

A second essential constituent of cosmetic compositions according to the invention is the oxidant a2). With regard to the desired cosmetic effect of the cosmetic preparation a), it has proven to be advantageous if the proportion by weight of the oxidant a2) in relation to the total weight of the cosmetic preparation a) is 0.5 to 15 wt %, preferably 1.0 to 12 wt %.

One preferred oxidant a2) is peroxydisulfate. Preferred peroxydisulfates to be used are the alkali metal and ammonium peroxydisulfates, preferably sodium peroxydisulfate, potassium peroxydisulfate and ammonium peroxydisulfate, in particular sodium peroxydisulfate and potassium peroxydisulfate, very particular preference being given to potassium peroxydisulfate.

One very particularly preferred oxidant a2) is hydrogen peroxide. In one preferred embodiment, the cosmetic preparation a) is an aqueous hydrogen peroxide solution, wherein the cosmetic preparation a) includes, in relation to the total weight of the preparation, preferably 1 to 15 wt %, particularly preferably 2 to 12 wt % hydrogen peroxide, calculated as 100% $H_2O_2$.

Besides the cosmetic preparation a), the cosmetic products according to the invention further comprise a flash evaporation device. In the context of the present application, the expression "flash evaporation" refers to the creation of vapor as the pressure is lowered in a closed chamber filled with liquid, said chamber being at an overpressure (relative to the surrounding environment). Such an overpressure can be generated for example by heating a quantity of the cosmetic preparation a) in a closed chamber to a temperature $T_1$. At a given temperature $T_1$, the liquid in the closed chamber has a saturation pressure $p_1$. If the closed chamber is opened for example by means of a valve to a relaxation chamber which is not at an overpressure and which is at the pressure $p_0 < p_1$, the pressure in the previously closed chamber decreases and the cosmetic preparation a), or the solvent or portions of said solvent included in the cosmetic preparation, evaporates as the new pressure level spreads. The resulting vapor or spray mist can be used to apply specific cosmetic preparations.

Therefore, if the cosmetic preparation a) is heated in a closed chamber starting from standard conditions ($T_0=25°$ C., $p_0=1000$ bar), this results in an increased pressure of the cosmetic preparation a) as well as an increased temperature. This increased pressure can be relieved in a relaxation chamber to a pressure $p_0$, for example the ambient air pressure ($p_0=1000$ bar), as a result of which an at least partial evaporation of the cosmetic preparation a) is achieved.

The cosmetic preparation a) may be relieved of pressure directly in the chamber in which it was previously heated. Alternatively, however, the heated cosmetic preparation a) at overpressure may also be transported, after heating, into a second chamber in which the pressure is then relieved.

In other words, flash evaporation is a method in which the cosmetic preparation a) is heated in a closed container by means of a heating device to temperatures above the ambient temperature, whereby a pressure above the ambient pressure is generated in the container, and the heated and pressurized cosmetic preparation a) is then released from the container into the environment.

A flash evaporation device is accordingly a device which comprises a container and a heating device and which is designed in such a way that a cosmetic preparation a) in the closed container can be heated by means of the heating device to temperatures above the ambient temperature so that a pressure above the ambient pressure is generated in the container and the heated and pressurized cosmetic preparation a) can be released from the container into the environment.

At the same time as or after the pressure relief, the cosmetic preparation a) can be fed to a nozzle, by means of which for example properties of the vapor or spray mist produced by the flash evaporation can be influenced, in particular the droplet size or the droplet density but also the spray width and the shape of the spray cone. The use of nozzles, preferably atomizing nozzles, is therefore preferred. The specific nozzle type or the specific nozzle design is defined in a targeted manner as a function of the respective spray mist properties.

To sum up, a preferred flash evaporation device has
b1) a container b1) which can be closed and opened by means of a valve and which defines the closed interior in which the cosmetic preparation can be accommodated,
b2) a heating device b2) which makes it possible to heat a cosmetic preparation located in the container b1).

Particular preference is given to the use of an additional nozzle b3) which enables an atomization of the cosmetic preparation a) escaping from the container. As an alternative to a valve, use can also be made of a closing element of comparable effect which is able to close or expose an associated opening in the container by means of corresponding change in position.

One preferred subject matter of the present invention is a cosmetic product comprising
a) a cosmetic preparation including, in relation to the total weight of the preparation,
   a1) 60 to 94 wt % polar solvent;
   a2) 0.1 to 20 wt % oxidant;
b) a device for flash-evaporating the cosmetic preparation a), wherein the flash evaporation device comprises a container b1) and a heating device b2 and is designed in such a way that
   the cosmetic preparation a) can be accommodated in the interior of the container b1),
   the interior of the container b1) which is at least partially filled with the cosmetic preparation a) can be closed,
   the cosmetic preparation a) in the closed interior of the container b1) can be heated by means of the heating device b2), the pressure thereby being increased.

One particularly preferred subject matter of the present invention is therefore a cosmetic product comprising
a) a cosmetic preparation including, in relation to the total weight of the preparation,
   a1) 60 to 94 wt % polar solvent;
   a2) 0.1 to 20 wt % oxidant;
b) a device for flash-evaporating the cosmetic preparation a), comprising
   b1) a container b1) which can be closed and opened by means of a valve,
   b2) a heating device which makes it possible to heat a cosmetic preparation located in the container b1),
   b3) a nozzle b3) which enables atomization of the cosmetic preparation a).

In other words, one particularly preferred subject matter of the present invention is a cosmetic product comprising
a) a cosmetic preparation including, in relation to the total weight of the preparation,
   a1) 60 to 94 wt % polar solvent;
   a2) 0.1 to 20 wt % oxidant;

b) a device for flash-evaporating the cosmetic preparation a), wherein the flash evaporation device comprises a container b1) and a heating device b2) and is designed in such a way that the cosmetic preparation a) can be accommodated in the interior of the container b1), the interior of the container b1) which is at least partially filled with the cosmetic preparation a) can be closed, the cosmetic preparation a) in the closed interior of the container b1) can be heated by means of the heating device b2), the pressure thereby being increased, the heated cosmetic preparation a) can be released from the interior of the container b1) into the environment, the pressure thereby being reduced.

The container b1) in which the cosmetic preparation is heated is designed in such a way as to make it possible to close said container fully with respect to the surrounding environment during the heating of the cosmetic preparation a) and to open it after the heating in order to enable the flash evaporation of the cosmetic preparation a). This can be ensured for example by a flow control component, in particular a valve.

The container b1) in which the cosmetic preparation is heated is preferably in contact with a further container, from which the quantity of the cosmetic preparation intended for the flash evaporation is transferred into the container b1) prior to heating. The access between this storage container and the container b1) can be opened and closed by way of a suitable device, for example a valve. This further container is preferably designed in the form of a storage container, that is to say it preferably includes a multiple of, for example more than ten times, preferably more than fifty times, the quantity of the cosmetic preparation necessary for an evaporation operation. In other words, the further container/storage container preferably has a multiple, for example more than ten times the volume, preferably more than twenty times and in particular more than fifty times the volume of the container b1).

Another particularly preferred subject matter of the present invention is therefore a cosmetic product comprising a) a cosmetic preparation including, in relation to the total weight of the preparation,
  a1) 60 to 94 wt % polar solvent;
  a2) 0.1 to 20 wt % oxidant;
b) a device for flash-evaporating the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least twenty times and in particular at least fifty times the volume of the container b1).

The storage container is not a pressure container, and the cosmetic composition located in the storage container is not pressurized; in other words, the pressure in the interior of the storage container corresponds to the ambient pressure (also air pressure or atmospheric pressure). Such cosmetic products thus comprise no propellants for example. In addition, the cosmetic product does not have a pump device suitable for releasing or spraying the cosmetic preparation into the environment without the action of the flash evaporation device.

One very particularly preferred subject matter of the present invention is therefore a cosmetic product comprising a) a cosmetic preparation including, in relation to the total weight of the preparation,
  a1) 60 to 94 wt % polar solvent;
  a2) 0.1 to 20 wt % oxidant;
b) a device for flash-evaporating the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least fifty times the volume of the container b1);
  the pressure in the interior of the storage container corresponds to the ambient pressure.

One very particularly preferred subject matter of the present invention is therefore a cosmetic product comprising a) a cosmetic preparation including, in relation to the total weight of the preparation,
  a1) 60 to 94 wt % polar solvent;
  a2) 0.1 to 20 wt % oxidant;
b) a device for flash-evaporating the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least fifty times the volume of the container b1);
  the pressure in the interior of the storage container corresponds to the ambient pressure and the cosmetic product does not include a propellant.

Preference is also given to cosmetic products comprising a) a cosmetic preparation including, in relation to the total weight of the preparation,
  a1) 60 to 94 wt % polar solvent;
  a2) 0.1 to 20 wt % oxidant;

b) a device for flash-evaporating the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least fifty times the volume of the container b1);
  the pressure in the interior of the storage container corresponds to the ambient pressure,
  wherein the cosmetic product does not include a pump device suitable for releasing or spraying the cosmetic preparation a) without the action of the flash evaporation device.

To sum up, one particularly preferred subject matter of the present invention is therefore a cosmetic product comprising
a) a cosmetic preparation including, in relation to the total weight of the preparation,
  a1) 60 to 94 wt % polar solvent;
  a2) 0.1 to 20 wt % oxidant;
b) a device for flash-evaporating the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least fifty times the volume of the container b1);
  the pressure in the interior of the storage container corresponds to the ambient pressure and the cosmetic product does not include a propellant,
  wherein the cosmetic product does not include a pump device suitable for releasing or spraying the cosmetic preparation a) without the action of the flash evaporation device.

Besides the two constituents a1) and a2) described above, the cosmetic preparations a) according to the invention may include further active ingredients or auxiliaries, particular preference being given to those active ingredients or auxiliaries which improve the ease of preparation, the ease of application and/or the cosmetic effect of cosmetic preparations according to the invention.

The anionic surfactants a3) are a first preferred constituent of the cosmetic preparations a). With regard to the ease of application and the cosmetic effect, it is preferred if the cosmetic preparation a) includes, in relation to the total weight of the preparation, 0.1 to 6.0 wt %, preferably 0.2 to 4.0 wt % and in particular 0.5 to 3.0 wt % anionic surfactant a3).

In the context of the invention, anionic surfactants are all anionic surface-active substances suitable for use on the human body. These are characterized by a water-solubilizing anionic group, such as for example a carboxylate, sulfate, sulfonate or phosphate group, and a lipophilic alkyl group having around 8 to 30 C atoms. In addition, glycol or polyglycol ether groups, ester, ether and amide groups and also hydroxyl groups may be included in the molecule. Examples of such anionic surfactants are, in each case in the form of the sodium, potassium and ammonium salts and the mono-, di- and trialkanolammonium salts having 2 to 4 C atoms in the alkanol group, linear and branched fatty acids having 8 to 30 C atoms (soaps); ether carboxylic acids, in particular of the formula $RO(CH_2CH_2O)_xCH_2COOH$, in which R is a linear alkyl group having 8 to 30 C atoms and x=0 or 1 to 16; acyl sarcosides; acyl taurides; acyl isethionates; sulfosuccinic acid mono- and dialkyl esters and sulfosuccinic acid monoalkyl polyoxyethyl esters; linear alkane sulfonates; linear α-olefin sulfonates; sulfonates of unsaturated fatty acids; α-sulfo-fatty acid methyl esters of fatty acids; alkyl sulfates and alkyl ether sulfates, in particular of the formula $RO(CH_2CH_2O)_xSO_3H$, in which R is a linear alkyl group having 8 to 30 C atoms and x is 0 or a number from 1 to 12; mixtures of surface-active hydroxysulfonates; sulfated hydroxyalkylpolyethylene and/or hydroxyalkylenepropylene glycol ethers; esters of tartaric acid and citric acid with alcohols; alkyl and/or alkenyl ether phosphates of the formula $RO(C_2H_4O)_xP(\!=\!O)(OH)(OR')$, in which R is an aliphatic, optionally unsaturated hydrocarbon residue having 8 to 30 carbon atoms, R' is hydrogen, a residue $(CH_2CH_2O)_yR$ and x and y independently of one another are a number from 1 to 10; sulfated fatty acid alkylene glycol esters of the formula $RC(O)O(alkO)_nSO_3H$, in which R is a linear or branched, aliphatic, saturated and/or unsaturated alkyl residue having 6 to 22 C atoms, alk is $CH_2CH_2$, $CHCH_3CH_2$ and/or $CH_2CHCH_3$ and n is a number from 0.5 to 5; and monoglyceride sulfates and monoglyceride ether sulfates. Particularly preferably Preferred anionic surfactants are fatty acids, alkyl sulfates, alkyl ether sulfates and ether carboxylic acids having 10 to 20 C atoms in the alkyl group and up to 16 glycol ether groups in the molecule. Particular preference is given to $C_8$-$C_{20}$ alkyl sulfates, in particular sodium cetearyl sulfate and sodium lauryl sulfate, and $C_8$-$C_{20}$ alkyl ether sulfates having 2 to 12, preferably 2 to 4 ethylene oxide groups, in particular sodium lauryl ether sulfate (INCI: Sodium Laureth Sulfate).

The nonionic surfactants a4) form a second group of preferred constituents of the cosmetic preparation a). Cosmetic products in which the cosmetic preparation a) includes, in relation to the total weight of the preparation, 0.1 to 6.0 wt %, preferably 0.2 to 4.0 wt % and in particular 0.5 to 3.0 wt % nonionic surfactant a4) are characterized by good application properties and a good cosmetic effect.

Preferred nonionic surfactants are PEG derivatives of hydrogenated castor oil, which are available for example under the name PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil, PEG-40 Hydrogenated Castor Oil or PEG-60 Hydrogenated Castor Oil. According to the invention, particular preference is given to nonionic surfactants selected from the group consisting of PEG derivatives of hydrogenated castor oil, particularly preferably from the group consisting of PEG-40 Hydrogenated Castor Oil and PEG-60 Hydrogenated Castor Oil.

The fatty substances a5) form a third group of preferred constituents of the cosmetic preparation a), wherein the proportion by weight of these fatty substances in relation to the total weight of the cosmetic preparation a) is preferably 1.0 to 25 wt %, more preferably 2.0 to 22 wt % and in particular 5.0 to 20 wt %.

The fatty substances a5) may be in solid or liquid form under normal conditions. The waxes form a first group of preferred fatty substances a5). The wax may be of natural or synthetic origin. Preferred waxes melt above 40° C., particularly preferably above 50° C., in particular at temperatures between 50° C. and 90° C.

As the wax, use may be made according to the invention of solid paraffins or isoparaffins, plant waxes such as candelilla wax, carnauba wax, esparto grass wax, Japan wax, cork wax, sugar cane wax, ouricury wax, montan wax, sunflower wax, fruit waxes and animal waxes, such as for example beeswax and other insect waxes, spermaceti, shellac wax, wool wax and uropygial grease, also mineral waxes, such as for example ceresin and ozokerite, or petrochemical waxes, such as for example petrolatum, paraffin waxes, microwaxes of polyethylene or polypropylene, and polyethylene glycol waxes. It may be advantageous to use hydrogenated or hardened waxes. It is also possible to use chemically modified waxes, in particular the hard waxes, for example montan ester waxes, sasol waxes and hydrogenated jojoba waxes.

Also suitable are the triglycerides of saturated and optionally hydroxylated C16-30 fatty acids, such as for example hardened triglyceride fats (hydrogenated palm oil, hydrogenated coconut oil, hydrogenated castor oil), glyceryl tribehenate or glyceryl tri-12-hydroxystearate, also synthetic full esters of fatty acids and glycols (for example Syncrowachs®) or polyols having 2-6 C atoms, fatty acid monoalkanolamides having a C12-22 acyl residue and a C2-4 alkanol residue, esters of saturated and/or unsaturated, branched and/or unbranched alkanecarboxylic acids having a chain length of 1 to 80 C atoms, and saturated and/or unsaturated, branched and/or unbranched alcohols having a chain length of 1 to 80 C atoms, including for example synthetic fatty acid fatty alcohol esters such as stearyl stearate or cetyl palmitate, esters of aromatic carboxylic acids, dicarboxylic acids or hydroxycarboxylic acids (for example 12-hydroxystearic acid) and saturated and/or unsaturated, branched and/or unbranched alcohols having a chain length of 1 to 80 C atoms, lactides of long-chain hydroxycarboxylic acids, and full esters of fatty alcohols and di- and tricarboxylic acids, for example dicetyl succinate or dicetyl/stearyl adipate, as well as mixtures of said substances.

The wax components may also be selected from the group consisting of esters of saturated, unbranched alkanecarboxylic acids having a chain length of 14 to 44 C atoms and saturated, unbranched alcohols having a chain length of 14 to 44 C atoms, provided that the wax component or the totality of the wax components are solid at room temperature. The wax components may be selected for example from the group consisting of C16-36 alkyl stearates, C10-40 alkyl stearates, C2-40 alkyl isostearates, C20-40 dialkyl esters of dimer acids, C18-38 alkyl hydroxystearoyl stearates, C20-40 alkyl erucates; use can also be made of C30-50 alkyl beeswax and cetearyl behenate. Silicone waxes, for example stearyl trimethylsilane/stearyl alcohol, are also possibly advantageous. Preferred wax components are the esters of saturated, monohydric C20-C60 alcohols and saturated C8-C30 monocarboxylic acids, particular preference being given to a C20-C40 alkyl stearate which is available under the name Kesterwachs® K82H from the company Koster Keunen Inc. The wax or the wax components should be solid at 25° C. but melt in the range from 35 to 95° C., preference being given to a range from 45 to 85° C.

Further preferred wax components are fatty alcohols. As fatty alcohols, use may be made for example of stearyl alcohol, cetyl alcohol, lauryl alcohol, myristyl alcohol, arachidyl alcohol, caprylic alcohol, capric alcohol and behenyl alcohol.

The wax is preferably selected from beeswax (Cera Alba), carnauba wax, candelilla wax, montan wax, cetyl palmitate, microcrystalline waxes (microcrystalline paraffins) and mixtures thereof. Particular preference is given to the use of a fatty substance a5) from the group consisting of beeswax (Cera Alba), carnauba wax and microcrystalline waxes (microcrystalline paraffins).

Natural, chemically modified and synthetic waxes can be used alone or in combination. The teaching according to the invention thus also encompasses the combined use of multiple waxes. Furthermore, a number of wax mixtures, optionally in admixture with further additives, are also commercially available. Those under the names "Spezialwachs 7686 OE" (a mixture of cetyl palmitate, beeswax, microcrystalline wax and polyethylene having a melting range of 73-75° C., manufacturer: Kahl & Co), Polywax® GP 200 (a mixture of stearyl alcohol and polyethylene glycol stearate having a melting point of 47-51° C.; manufacturer: Croda) and "Weichceresin® FL 400" (a vaseline/vaseline oil/wax mixture having a melting point of 50-54° C.; manufacturer: Parafluid Mineralolgesellschaft) are examples of mixtures which are used with preference according to the invention. Another particularly preferred mixture of waxes a2) comprises beeswax and carnauba wax, optionally in combination with microcrystalline wax.

The oils form a second group of fatty substances a5) which are preferred according to the invention. The oils may be of natural or synthetic origin. Preferred oils melt below 10° C., particularly preferably below 0° C.

Preferred cosmetic preparations a) according to the invention include at least one oil from the group consisting of silicone oils. The group consisting of silicone oils includes in particular the dimethicones (also encompassing the cyclomethicones), the amino-functional silicones and the dimethiconols. The dimethicones may be linear or branched and also cyclic or cyclic and branched. Suitable silicone oils or silicone gums are in particular dialkyl- and alkylarylsiloxanes, such as for example dimethylpolysiloxane and methylphenylpolysiloxane, as well as the alkoxylated, quaternized or anionic derivatives thereof.

Further preferred cosmetic preparations a) according to the invention include at least one oil from the group consisting of ester oils, that is to say esters of C6-C30 fatty acids with C2-C30 fatty alcohols, preferably monoesters of the fatty acids with alcohols having 2 to 24 C atoms, such as for example isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), hexyl laurate (Cetiol® A), di-n-butyl adipate (Cetiol® B), myristyl myristate (Cetiol® MM), cetearyl isononanoate (Cetiol® SN), decyl oleate (Cetiol® V).

The group consisting of oils also includes the following preferred substances:
- liquid paraffin oils, isoparaffin oils and synthetic hydrocarbons as well as di-n-alkyl ethers having a total of 12 to 36 C atoms, in particular 12 to 24 C atoms, such as for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether as well as di-tert-butyl ether, diisopentyl ether, di-3-ethyl decyl ether, tert-butyl n-octyl ether, isopentyl n-octyl ether and 2-methyl pentyl n-octyl ether,
- natural (plant) oils, triglycerides and mixtures of triglycerides can be used. Preferred natural oils are soybean oil, rapeseed oil, orange oil, coconut oil, (sweet) almond oil, walnut oil, peach kernel oil, apricot kernel oil, avocado oil, tea tree oil, sesame oil, sunflower oil, tsubaki oil, evening primrose oil, rice bran oil, palm kernel oil, mango seed oil, meadowfoam seed oil, thistle oil, macadamia nut oil, grape seed oil, amaranth seed oil, argan oil, bamboo oil, olive oil, wheat germ oil, pumpkin seed oil, mallow oil, hazelnut oil, safflower oil, canola oil, sasanqua oil, jojoba oil, rambutan oil, cocoa butter and shea butter,
- dicarboxylic acid esters such as di-n-butyl adipate, di-(2-ethylhexyl) adipate, di-(2-ethylhexyl) succinate and diisotridecyl acelaate as well as diol esters such as ethylene glycol dioleate, ethylene glycol diisotridecanoate, propylene glycol di-(2-ethylhexanoate), propylene glycol diisostearate, propylene glycol dipelargonate, butane diol diisostearate, neopentyl glycol dicaprylate,
- symmetrical, unsymmetrical or cyclic esters of carbonic acid with fatty alcohols, for example described in DE-OS 197 56 454, glycerol carbonate or dicaprylyl carbonate (Cetiol® CC),
- trifatty acid esters of saturated and/or unsaturated linear and/or branched fatty acids with glycerol,
- polyol fatty acid esters, such as for example the commercial product Hydagen® HSP (Cognis) or Sovermol types (Cognis), from fatty acid and/or fatty acid derivatives and polyols having at least two hydroxyl groups, and having a carbon chain of 2 to 30 carbon atoms, such as for example fatty acid esters of trimethylolpropane.

Particular preference is given to the use of a fatty substance a5) from the group consisting of silicone oils, paraffin oils, plant oils and ester oils, preferably from the group consisting of silicone oils and paraffin oils.

The thickeners a6) form a fourth group of preferred constituents of the cosmetic preparation a).

Preferred thickeners are selected from the group consisting of polymeric organic thickeners. The polymeric organic thickeners may be crosslinked or non-crosslinked.

With regard to the ease of preparation, the ease of application and the cosmetic effect of cosmetic compositions according to the invention, it has proven to be advantageous if the proportion by weight of the thickener a6) in relation to the total weight of the cosmetic preparation a) is 0.1 to 12 wt %, preferably 0.2 to 10 wt % and in particular 0.5 to 8.0 wt %.

Examples of customary thickeners a6) are polymeric thickeners having the INCI names Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylic Acid/Acrylonitrogens Copolymer, Agar, Agarose, *Alcaligenes* Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, *Astragalus* Gummifer Gum, Attapulgite, *Avena Sativa* (Oat) Kernel Flour, Bentonite, Butoxy Chitosan, *Caesalpinia Spinosa* Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, *Ceratonia Siliqua* Gum, Cetyl Hydroxyethylcellulose, Cholesterol/HDI/Pullulan Copolymer, Cholesteryl Hexyl Dicarbamate Pullulan, Cyamopsis Tetragonoloba (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine Soja* (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, *Sclerotium* Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, *Sterculia Urens* Gum, Synthetic Fluorphlogopite, Tamarindus Indica Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, *Zea Mays* (Corn) Starch.

Besides the above-described ingredients a1), a2) and a3) to a6), the cosmetic products according to the invention may include further active ingredients, auxiliaries and care substances.

The composition of some particularly preferred cosmetic preparations according to the invention can be seen in the following tables (unless indicated otherwise, figures specified in wt % are based on the total weight of the cosmetic product). With regard to further preferred embodiments of these particularly preferred compositions, what has been stated above in relation to the cosmetic preparations a) according to the invention applies, mutatis mutandis.

|  | Formula 1 | Formula 2 | Formula 3 | Formula 4 | Formula 5 |
| --- | --- | --- | --- | --- | --- |
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Optional additives | ad 100 | ad 100 | ad 100 | ad 100 | ad 100 |

|  | Formula 6 | Formula 7 | Formula 8 | Formula 9 | Formula 10 |
| --- | --- | --- | --- | --- | --- |
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Optional additives | ad 100 | ad 100 | ad 100 | ad 100 | ad 100 |

|  | Formula 11 | Formula 12 | Formula 13 | Formula 14 | Formula 15 |
| --- | --- | --- | --- | --- | --- |
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Optional additives | ad 100 | ad 100 | ad 100 | ad 100 | ad 100 |

|  | Formula 16 | Formula 17 | Formula 18 | Formula 19 | Formula 20 |
| --- | --- | --- | --- | --- | --- |
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Optional additives | ad 100 | ad 100 | ad 100 | ad 100 | ad 100 |

|  | Formula 21 | Formula 22 | Formula 23 | Formula 24 | Formula 25 |
| --- | --- | --- | --- | --- | --- |
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Nonionic surfactant a4) | 0.1 to 6.0 | 0.2 to 4.0 | 0.5 to 3.0 | 0.5 | 1.5 |
| Optional additives | ad 100 | ad 100 | ad 100 | ad 100 | ad 100 |

|  | Formula 26 | Formula 27 | Formula 28 | Formula 29 | Formula 30 |
| --- | --- | --- | --- | --- | --- |
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Nonionic surfactant a4) | 0.1 to 6.0 | 0.2 to 4.0 | 0.5 to 3.0 | 0.5 | 1.5 |
| Optional additives | ad 100 | ad 100 | ad 100 | ad 100 | ad 100 |

|  | Formula 31 | Formula 32 | Formula 33 | Formula 34 | Formula 35 |
| --- | --- | --- | --- | --- | --- |
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Fatty substance a5) | 1.0 to 25 | 2.0 to 22 | 0.5 to 20 | 2.0 | 17 |
| Optional additives | ad 100 | ad 100 | ad 100 | ad 100 | ad 100 |

-continued

|  | Formula 36 | Formula 37 | Formula 38 | Formula 29 | Formula 40 |
|---|---|---|---|---|---|
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Fatty substance a5) | 1.0 to 25 | 2.0 to 22 | 0.5 to 20 | 2.0 | 17 |
| Optional additives | ad 100 | ad 100 | ad 100 | ad 100 | ad 100 |

|  | Formula 41 | Formula 42 | Formula 43 | Formula 44 | Formula 45 |
|---|---|---|---|---|---|
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Thickener a6) | 0.1 to 12 | 0.2 to 10 | 0.5 to 8.0 | 5.0 | 0.6 |
| Optional additives | ad 100 | ad 100 | ad 100 | ad 100 | ad 100 |

|  | Formula 46 | Formula 47 | Formula 48 | Formula 49 | Formula 50 |
|---|---|---|---|---|---|
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Thickener a6) | 0.1 to 12 | 0.2 to 10 | 0.5 to 8.0 | 5.0 | 0.6 |
| Optional additives | ad 100 | ad 100 | ad 100 | ad 100 | ad 100 |

|  | Formula 51 | Formula 52 | Formula 53 | Formula 54 | Formula 55 |
|---|---|---|---|---|---|
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Nonionic surfactant a4) | 0.1 to 6.0 | 0.2 to 4.0 | 0.5 to 3.0 | 0.5 | 1.5 |
| Optional additives | ad 100 | ad 100 | ad 100 | ad 100 | ad 100 |

|  | Formula 56 | Formula 57 | Formula 58 | Formula 59 | Formula 60 |
|---|---|---|---|---|---|
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Nonionic surfactant a4) | 0.1 to 6.0 | 0.2 to 4.0 | 0.5 to 3.0 | 0.5 | 1.5 |
| Optional additives | ad 100 | ad 100 | ad 100 | ad 100 | ad 100 |

|  | Formula 61 | Formula 62 | Formula 63 | Formula 64 | Formula 65 |
|---|---|---|---|---|---|
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Fatty substance a5) | 1.0 to 25 | 2.0 to 22 | 0.5 to 20 | 2.0 | 17 |
| Optional additives | ad 100 | ad 100 | ad 100 | ad 100 | ad 100 |

|  | Formula 66 | Formula 67 | Formula 68 | Formula 69 | Formula 70 |
|---|---|---|---|---|---|
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Fatty substance a5) | 1.0 to 25 | 2.0 to 22 | 0.5 to 20 | 2.0 | 17 |
| Optional additives | ad 100 | ad 100 | ad 100 | ad 100 | ad 100 |

|  | Formula 71 | Formula 72 | Formula 73 | Formula 74 | Formula 75 |
|---|---|---|---|---|---|
| Polar solvent a1) | 65 to 90 | 70 to 88 | 75 to 85 | 84 | 71 |
| Oxidant a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Thickener a6) | 0.1 to 12 | 0.2 to 10 | 0.5 to 8.0 | 5.0 | 0.6 |
| Optional additives | ad 100 | ad 100 | ad 100 | ad 100 | ad 100 |

|  | Formula 76 | Formula 77 | Formula 78 | Formula 79 | Formula 80 |
|---|---|---|---|---|---|
| Polar solvent a1) | 65 to 90 | 70 to 88 | 75 to 85 | 84 | 71 |
| Hydrogen peroxide a2) | 0.1 to 20 | 0.5 to 15 | 1.0 to 12 | 5.0 | 6.0 |
| Anionic surfactant a3) | 0.1 to 6.0 | 0.2 to 4.0 | 0.5 to 3.0 | 2.0 | 1.0 |
| Thickener a6) | 0.1 to 12 | 0.2 to 10 | 0.5 to 8.0 | 5.0 | 0.6 |
| Optional additives | ad 100 | ad 100 | ad 100 | ad 100 | ad 100 |

Very particularly preferred cosmetic preparations include, besides the above-described constituents a1) to a6), only small amounts of further active ingredients and auxiliaries. On account of their ease of preparation and good cosmetic effect, particular preference is given to cosmetic preparations which are characterized in that the proportion by weight of the constituents a1), a2) and, if present, the optional constituents a3) to a6) in relation to the total weight of the cosmetic preparation is at least 86 wt %, preferably at least 90 wt % and in particular at least 94 wt %.

As stated in the introduction, the cosmetic preparations a) according to the invention are particularly suitable for application by means of a flash evaporation device. A further subject matter of the present application is therefore the use of a cosmetic preparation a) including, in relation to the total weight of the preparation,
a1) 60 to 94 wt % polar solvent;
a2) 0.1 to 20 wt % oxidant;
as a process material in a flash evaporation device.

Another subject matter of the present invention is the use of a product according to the invention for applying a cosmetic preparation a) to keratinous fibers, in particular human hair, or for changing the color of keratinous fibers, in particular human hair.

A method for changing the color of keratinous fibers, in particular human hair, in which a cosmetic preparation a) including, in relation to the total weight of the preparation,
a1) 60 to 94 wt % polar solvent;
a2) 0.1 to 20 wt % oxidant;
is applied to the keratinous fibers by means of a flash evaporation device, forms a further subject matter of the present application. By means of the flash evaporation device, the cosmetic preparation a) is preferably converted into a spray mist which is then applied to the keratinous fibers.

In order to achieve a sufficient spraying effect, the cosmetic preparation a) is preferably heated to temperatures above the boiling point of the polar solvent or solvent mixture included in the cosmetic preparation a).

If the polar solvent is water or if the solvent mixture has a water content above 50 wt % (in relation to the total weight of the solvent mixture), the cosmetic preparation is preferably heated to temperatures above 100° C., more preferably to temperatures of from 100° C. to 240° C., particularly preferably to temperatures of from 140° C. to 160° C.

In cases where the polar solvent is water or a solvent mixture having a water content above 50 wt % (in relation to the total weight of the solvent mixture), the overpressure achieved as a result of heating the cosmetic preparation a) is preferably between 1.1 and 8 bar, more preferably between 1.2 and 4 bar.

One preferred subject matter of the application is a method for changing the color of keratinous fibers, in particular human hair, in which a cosmetic preparation a) including, in relation to the total weight of the preparation,
a1) 60 to 94 wt % polar solvent;
a2) 0.1 to 20 wt % oxidant;
is applied to the keratinous fibers by means of a flash evaporation device, wherein,
from a storage container in the interior of which a pressure corresponding to the ambient pressure prevails, a partial quantity of the cosmetic preparation a) located in this storage container is transferred into a container b1);
then the access between the storage container and the container b1) is interrupted by a flow control component, by means of which the flow of the cosmetic preparation a) from the storage container into the container b1) can be interrupted;
then the cosmetic preparation a) located in the container b1) which is sealed off from the environment is heated by means of a heating device so that the pressure in the interior of the container b1) increases to values above the ambient pressure, preferably to values between 1.1 and 8 bar, in particular to values between 1.2 and 4 bar;
then the container b1) which is at a pressure above the ambient pressure is opened in such a way as to enable at least a partial quantity, preferably at least 50 wt %, more preferably at least 80 wt % and in particular at least 90 wt %, of the cosmetic preparation located in the container b1) to be released from the container b1) into the environment, thereby reducing the pressure prevailing in the container b1) at the time of opening of the container.

The release of the cosmetic preparation a) into the environment preferably takes place by forming a spray mist of the cosmetic preparation a).

The cosmetic preparation a) released from the container b1) is preferably applied to keratinous fibers, in particular human hair.

Particular preference is given to methods during which the cosmetic preparation released from the container b1) is conducted through a nozzle before being applied to the keratinous fibers.

With regard to further preferred embodiments of the uses according to the invention and of the method according to the invention, what has been stated above in relation to the cosmetic preparations a) according to the invention and in relation to the flash expansion device b) applies, mutatis mutandis.

The products, uses and methods according to the invention, and some preferred embodiments thereof, are characterized in summary by the following points:
A cosmetic product comprising
a) a cosmetic preparation including, in relation to the total weight of the preparation,
 a1) 60 to 94 wt % polar solvent;
 a2) 0.1 to 20 wt % oxidant;
b) a device for flash-evaporating the cosmetic preparation a).

The cosmetic product according to point 1, characterized in that the flash evaporation device comprises a container b1) and a heating device b2) and is designed in such a way that
 the cosmetic preparation a) can be accommodated in the interior of the container b1),
 the interior of the container b1) at least partially filled with the cosmetic preparation a) can be closed,
 the cosmetic preparation a) in the closed interior of the container b1) can be heated by means of the heating device b2), the pressure thereby being increased,
 the heated cosmetic preparation a) can be released from the interior of the container b1) into the environment, the pressure thereby being reduced.

The cosmetic product according to any of the preceding points, characterized in that the proportion by weight of the polar solvent a1) in relation to the total weight of the cosmetic preparation a) is 65 to 90 wt %, preferably 70 to 88 wt % and in particular 75 to 85 wt %.

The cosmetic product according to any of the preceding points, characterized in that the polar solvent a1) has a boiling point (20° C., 1013 mbar) between 50 and 110° C., preferably between 70 and 105° C.

The cosmetic product according to any of the preceding points, characterized in that the polar solvent a1) is selected from the group consisting of water and ethanol.

The cosmetic product according to any of the preceding points, characterized in that the proportion by weight of water in relation to the total weight of the polar solvent a1) is more than 80 wt %, preferably more than 85 wt % and in particular more than 90 wt %.

The cosmetic product according to any of the preceding points, characterized in that the proportion by weight of the oxidant a2) in relation to the total weight of the cosmetic preparation a) is 0.5 to 15 wt %, preferably 1.0 to 12 wt %.

The cosmetic product according to any of the preceding points, characterized in that peroxydisulfate, preferably sodium peroxydisulfate or potassium peroxydisulfate, in particular potassium peroxydisulfate, is used as the oxidant a2).

The cosmetic product according to any of points 1 to 7, characterized in that hydrogen peroxide is used as the oxidant a2).

The cosmetic product according to any of the preceding points, characterized in that the cosmetic preparation a) includes, in relation to the total weight of the preparation, 0.1 to 6.0 wt %, preferably 0.2 to 4.0 wt % and in particular 0.5 to 3.0 wt % anionic surfactant a3).

The cosmetic product according to point 9, characterized in that the anionic surfactant a3) is selected from the group consisting of alkyl sulfates and alkyl ether sulfates.

The cosmetic product according to any of the preceding points, characterized in that the cosmetic preparation a) includes, in relation to the total weight of the preparation, 0.1 to 6.0 wt %, preferably 0.2 to 4.0 wt % and in particular 0.5 to 3.0 wt % nonionic surfactant a4).

The cosmetic product according to point 11, characterized in that the nonionic surfactant a4) is selected from the group consisting of PEG derivatives of hydrogenated castor oil, particularly preferably from the group consisting of PEG-40 Hydrogenated Castor Oil and PEG-60 Hydrogenated Castor Oil.

The cosmetic product according to any of the preceding points, characterized in that the cosmetic preparation a) includes, in relation to the total weight of the preparation, 1.0 to 25 wt %, preferably 2.0 to 22 wt % and in particular 5.0 to 20 wt % fatty substance a5).

The cosmetic product according to point 14, characterized in that the fatty substance a5) is selected from the group consisting of waxes.

The cosmetic product according to any of points 14 or 15, characterized in that the fatty substance a5) is selected from the group consisting of beeswax (Cera Alba), carnauba wax and microcrystalline waxes (microcrystalline paraffins).

The cosmetic product according to point 14, characterized in that the fatty substance a5) is selected from the group consisting of oils.

The cosmetic product according to any of points 14 or 17, characterized in that the fatty substance a5) is selected from the group consisting of silicone oils, paraffin oils, plant oils and ester oils, preferably from the group consisting of silicone oils and paraffin oils.

The cosmetic product according to any of the preceding points, characterized in that the cosmetic preparation a) includes, in relation to the total weight of the preparation, 0.1 to 12 wt %, preferably 0.2 to 10 wt % and in particular 0.5 to 8.0 wt % of a polymeric thickener a6).

The cosmetic product according to any of the preceding points, characterized in that the cosmetic preparation a) consists to a proportion of at least 86 wt %, preferably at least 90 wt % and in particular at least 94 wt % of the constituents a1) and a2) and, if present, the optional constituents a3) to a6), in relation to the total weight of the preparation.

The use of a cosmetic preparation a) including, in relation to the total weight of the preparation,
a) a cosmetic preparation including, in relation to the total weight of the preparation,
   a1) 60 to 94 wt % polar solvent;
   a2) 0.1 to 20 wt % oxidant;
as a process material in a flash evaporation device.

The use of a product according to any of points 1 to 20 for applying a cosmetic preparation a) to keratinous fibers, in particular human hair.

The use of a product according to any of points 1 to 20 for changing the color of keratinous fibers, in particular human hair.

A method for changing the color of keratinous fibers, in particular human hair, in which a cosmetic preparation a) including, in relation to the total weight of the preparation,
a1) 60 to 94 wt % polar solvent;
a2) 0.1 to 20 wt % oxidant;
is applied to the keratinous fibers by means of a flash evaporation device.

The method according to point 23, characterized in that,
  from a storage container in the interior of which a pressure corresponding to the ambient pressure prevails, a partial quantity of the cosmetic preparation a) located in this storage container is transferred into a container b1);
  then the access between the storage container and the container b1) is interrupted by a flow control component, by means of which the flow of the cosmetic preparation a) from the storage container into the container b1) can be interrupted;
  then the cosmetic preparation a) located in the container b1) which is sealed off from the environment is heated by means of a heating device so that the pressure in the interior of the container b1) increases to values above the ambient pressure, preferably to values between 1.1 and 8 bar, in particular to values between 1.2 and 4 bar;
  then the container b1) which is at a pressure above the ambient pressure is opened in such a way as to enable at least a partial quantity, preferably at least 50 wt %, more preferably at least 80 wt % and in particular at least 90 wt %, of the cosmetic preparation located in the container b1) to be released from the container b1) into the environment, thereby reducing the pressure prevailing in the container b1) at the time of opening of the container.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic product comprising:
   a) a cosmetic preparation comprising, in relation to the total weight of the preparation:
      a1) 60 to 94 wt % polar solvent, and
      a2) 0.1 to 20 wt % oxidant; and
   b) a device for flash-evaporating the cosmetic preparation a).

2. The cosmetic product according to claim 1, wherein the flash evaporation device comprises:
a container b1) and
a heating device b2) wherein,
the cosmetic preparation a) can be accommodated in the interior of the container b1),
the interior of the container b1) can be closed when at least partially filled with the cosmetic preparation a),
the cosmetic preparation a) in the closed interior of the container b1) can be heated by means of the heating device b2), the pressure thereby being increased, and
the heated cosmetic preparation a) can be released from the interior of the container b1) into the environment, the pressure thereby being reduced.

3. The cosmetic product according to claim 1, wherein the proportion by weight of the polar solvent a1) in relation to the total weight of the cosmetic preparation a) is 65 to 90 wt %.

4. The cosmetic product according to claim 1, wherein the polar solvent a1) is selected from the group consisting of water and ethanol.

5. The cosmetic product according to claim 1, wherein a proportion by weight of the oxidant a2) in relation to the total weight of the cosmetic preparation a) is 0.5 to 15 wt %.

6. The cosmetic product according to claim 1, wherein a peroxydisulfate is used as the oxidant a2).

7. The cosmetic product according to claim 1, wherein hydrogen peroxide is used as the oxidant a2).

8. A method of using a cosmetic preparation a) comprising flash evaporating cosmetic preparation a), wherein the cosmetic preparation a) comprises, in relation to the total weight of the preparation:
a1) 60 to 94 wt % polar solvent; and
a2) 0.1 to 20 wt % oxidant.

9. A method for changing the color of keratinous fibers, including:
applying to the keratinous fibers, by means of a flash evaporation device, a cosmetic preparation a) comprising, in relation to the total weight of the preparation:
a1) 60 to 94 wt % polar solvent; and
a2) 0.1 to 20 wt % oxidant.

10. The method according to claim 9, further comprising:
transferring a partial quantity of the cosmetic preparation a) from a storage container into a container b1), where the interior of the storage container is at ambient pressure;
obstructing flow between the storage container and the container b1) by a flow control component;
heating the sealed container b1) containing the cosmetic preparation a) using a heating device so that the pressure in the interior of the container b1) increases to between 1.1 and 8 bar; and
venting the container b1), which is at a pressure above the ambient pressure, such that at least 50 wt of the cosmetic preparation located in the container b1) is released from the container b1) into the environment.

11. The cosmetic product according to claim 1, wherein the device b) comprises a reservoir holding no less than 10 doses of cosmetic preparation a), wherein a dose is an volume of cosmetic preparation a) flash evaporated by the device at a time.

12. The cosmetic product according to claim 11, wherein the device b) further comprises a access between the reservoir and a heating chamber, wherein the heating chamber contains the cosmetic preparation a) during heating.

13. The cosmetic product according to claim 12, wherein the device b) outputs material from the heating chamber through a nozzle.

14. The cosmetic product according to claim 13, wherein the nozzle is an atomizing nozzle.

15. The cosmetic product according to claim 1, wherein the cosmetic preparation a) further comprises 0.1 to 6.0 wt % anionic surfactant a3), in relation to the total weight of the cosmetic preparation.

16. The cosmetic product according to claim 1, wherein the cosmetic preparation a) further comprises 0.1 to 6.0 wt % nonionic surfactant a4), in relation to the total weight of the cosmetic preparation.

17. The cosmetic product according to claim 16, wherein the nonionic surfactant a4 is polyglycolated-hydrogenated castor oil having 30 to 60 glycol units per molecule.

18. The cosmetic product according to claim 1, wherein the cosmetic preparation a) further comprises 5.0 to 20 wt % fatty substance a5), in relation to the total weight of the cosmetic preparation.

19. The cosmetic preparation according to claim 18, wherein the fatty substance is selected from the group consisting of: silicone oils, paraffin oils, plant oils, ester oils and mixtures thereof.

20. The cosmetic preparation according to claim 18, wherein the fatty substance is a silicone oil.

* * * * *